United States Patent
Vesto (10) Patent No.: US 9,202,388 B2
(45) Date of Patent: Dec. 1, 2015

(54) METHODS AND SYSTEMS FOR IMPROVING PATIENT ENGAGEMENT VIA MEDICAL AVATARS

(71) Applicant: General Electric Company, Schenectady, NY (US)

(72) Inventor: Guy Robert Vesto, Kildeer, IL (US)

(73) Assignee: General Electric Company, Schenectady, NY (US)

( * ) Notice: Subject to any disclaimer, the term of this patent is extended or adjusted under 35 U.S.C. 154(b) by 440 days.

(21) Appl. No.: 13/834,469

(22) Filed: Mar. 15, 2013

(65) Prior Publication Data

US 2014/0277678 A1 Sep. 18, 2014

(51) Int. Cl.
*G06F 19/00* (2011.01)
*G09B 23/30* (2006.01)
*G09B 23/28* (2006.01)

(52) U.S. Cl.
CPC ............... *G09B 23/30* (2013.01); *G09B 23/28* (2013.01)

(58) Field of Classification Search
CPC ............................. G09B 23/30; G09B 23/28
USPC .......................................................... 700/119
See application file for complete search history.

(56) References Cited

U.S. PATENT DOCUMENTS

| 8,908,943 | B2* | 12/2014 | Berry et al. ................ 382/128 |
| 8,992,232 | B2* | 3/2015 | Berry et al. ................ 434/267 |
| 2011/0072367 | A1* | 3/2011 | Bauer ........................... 715/757 |
| 2012/0280988 | A1* | 11/2012 | Lampotang et al. ......... 345/419 |

OTHER PUBLICATIONS

Peter Murray, "Surgeon Uses 3D Printer to Make Models of Bone" retrieved from the internet:>http://singularityhub.com/2011/11/15/surgeon-uses-3d-printer-to-make-models-of-bone-%E2%80%93-and-saves-hospital-bookoo-bucks/>, last visited on Jul. 26, 2013, 3 pages.

Madhumita Venkataramanan, "How 3D printing built a new face" retrieved from the internet:>http://www.wired.co.uk/magazine/archive/2012/07/start/how-3d-printing-built-a-new-face>, last visited on Jul. 26, 2013, 1 page.

(Continued)

*Primary Examiner* — Robert Fennema
*Assistant Examiner* — Sivalingam Sivanesan
(74) *Attorney, Agent, or Firm* — Hanley, Flight and Zimmerman, LLC (57) ABSTRACT

Certain examples provide systems, methods, and apparatus for patient care and support. An example three-dimensional printed model of a portion of a patient anatomy is to be formed for the patient based on image data obtained of the patient. The three-dimensional printed model includes an output device to provide an output from the three-dimensional printed model that is perceptible to the patient. The three-dimensional printed model includes a communication device to facilitate exchange of information between the three-dimensional printed model and one or more external systems. The three-dimensional printed model includes a controller to facilitate exchange of information, via the communication device, between the three-dimensional printed model and the one or more external systems. The controller is also to provide feedback to the patient via the output device with respect to a condition affecting the portion of the patient anatomy represented by the three-dimensional printed model via the output device.

20 Claims, 5 Drawing Sheets

(56) References Cited

OTHER PUBLICATIONS

Maria Koufali, "New 3D printing Techniques using MRI & CT Deliver Safer Surgery Training" retrieved from the internet: >http://nuhrise.org/2011/09/surgery-models-new-3d-printing-techniques-using-mri-ct-deliver-safer-surgery-training/>, last visited on Jul. 26, 2013, 4 pages.

Katie Scott, "3D-printed bones touted for surgical use in human within 10 years", retrieved from the internet:>http://www.wired.co.uk/news/archive/2011-11/30/3d-printed-bone>, last visited Jul. 26, 2013, 1 page.

"Medical Avatar", retrieved from the internet:>http://medicalavatar.com/:>, last visited Jul. 26, 2013, 4 pages.

* cited by examiner

Figure 5

METHODS AND SYSTEMS FOR IMPROVING PATIENT ENGAGEMENT VIA MEDICAL AVATARS

FIELD

The present invention generally relates to patient care and treatment. More specifically, the present invention relates to systems, methods, and apparatus to facilitate patient engagement in care and treatment of a condition through the use of a physical avatar associated with that condition.

BACKGROUND

The world's healthcare systems are in crisis. Developed countries have a finite amount of healthcare resources and high patient expectations; many also have aging populations. Their healthcare systems all too often provide inconsistent quality, too many preventable medical errors, and overtreatment resulting in unnecessary injuries and deaths. Patient dissatisfaction is a big issue. Healthcare organizations do not seem to understand "the patient experience." At the same time, patient engagement is viewed as a critical factor to begin solving the major challenges in healthcare. Patient engagement is defined as constructive collaborative relationships between patients, caregivers, and clinicians. For example, the Meaningful Use Stage 2 requirements developed by the Centers for Medicare and Medicaid Services (CMS) have a strong emphasis on patient engagement. However, without patient participation, there is no patient engagement. There have been numerous failed attempts at patient engagement due to lack of participation.

The most common approach to prior attempts at patient engagement has been in form of various web-based patient portals and personal health records. For example, Medicare's Blue Button initiative is a Web-based feature through which patients may easily and securely download their health information from doctors, insurers, pharmacies, or other health-related services and share it with health care providers and caregivers. Each of these efforts has had limited success especially with elderly patients and low-income patients who often need engagement the most. As a result, hospital readmissions increase.

BRIEF SUMMARY

Certain examples provide systems, methods, and apparatus for patient care and support.

Certain examples provide an apparatus including a three-dimensional printed model of a portion of a patient anatomy. The three-dimensional printed model is to be formed for the patient based on image data obtained of the patient. The example three-dimensional printed model includes an output device to provide an output from the three-dimensional printed model that is perceptible to the patient. The example three-dimensional printed model includes a communication device to facilitate exchange of information between the three-dimensional printed model and one or more external systems. The example three-dimensional printed model includes a controller to facilitate exchange of information, via the communication device, between the three-dimensional printed model and the one or more external systems. The example controller is also to provide feedback to the patient via the output device with respect to a condition affecting the portion of the patient anatomy represented by the three-dimensional printed model via the output device.

Certain examples provide a system including a three-dimensional printed avatar representing a portion of a patient anatomy. The example three-dimensional printed avatar is to be formed for the patient based on image data obtained of the patient. The example three-dimensional printed avatar includes an output device to provide an output from the three-dimensional printed avatar that is perceptible to the patient. The example three-dimensional printed avatar includes a communication device to facilitate exchange of information between the three-dimensional printed avatar and one or more external systems. The example three-dimensional printed avatar includes a controller to facilitate exchange of information, via the communication device, between the three-dimensional printed avatar and the one or more external systems. The example controller is also to provide feedback to the patient via the output device with respect to a condition affecting the portion of the patient anatomy represented by the three-dimensional printed avatar via the output device. The example three-dimensional printed avatar includes a remote services platform providing applications and platform services to form a virtual avatar corresponding to the three-dimensional printed avatar. The example remote services platform is to communicate with the three-dimensional printed avatar via a mobile device associated with the patient. The example remote services platform is to provide support for three-dimensional modeling, messaging with the patient, and integration with external systems.

Certain examples provide a tangible computer-readable storage medium including a set of instructions to be executed by a processor, the instructions, when executed, implementing a method. The example method includes generating three-dimensional model information to print a physical avatar on a three-dimensional printer. The example physical avatar is to model a portion of a particular patient's anatomy based on image data obtained of the particular patient. The example physical avatar is to include an output device to provide an output from the physical avatar that is perceptible to the patient. The example physical avatar is to include a communication device to facilitate exchange of information between the physical avatar and one or more external systems. The example physical avatar is to include a controller to facilitate exchange of information, via the communication device, between the physical avatar and the one or more external systems. The example method includes facilitating an exchange of information related to the patient between the physical avatar and the one or more external systems that provide a virtual avatar. The example virtual avatar is to provide messaging, information and patient participation tools to facilitate patient engagement in monitoring and treatment of a condition affecting the portion of the patient anatomy represented by the physical avatar. The example exchange of information is to include alerts provided by the output device in response to information from the virtual avatar.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Certain examples provide improved healthcare systems and methods to facilitate improved quality, reduced medical errors, reduced overtreatment, and improved patient satisfaction. Certain examples provide an improved patient experience and facilitate better patient engagement for constructive, collaborative relationships between patients, caregivers, and clinicians (e.g., Meaningful Use Stage 2). Certain examples provide a unique and fun approach at achieving patient engagement by stimulating patient participation through gamification and by leveraging three-dimensional (3D) printers and mobile devices.

Certain examples provide a tangible object for a patient to take home from a hospital or clinic to help the patient in education, treatment, monitoring, etc. For example, a 3D printed object can be made for the patient which recreates an internal organ that is representative of a disease from which the patient is suffering. The object is accompanied by a virtual electronic counterpart with which the patient can interact via a smart phone, tablet computer, laptop, handheld computer, etc. Certain examples provide systems and method for the patient to collaborate with a care team via the 3D object and a mobile device by leveraging Near Field Communication (NFC) technology and/or other wireless communication technology and an associated registry and context engine.

Certain examples help to alert and/or prompt the patient to comply with tasks in his or her treatment plan via the 3D printed object. Via the object, the patient can be encouraged and/or challenged via gamification (e.g. social games) that are specific to the disease and the patient's treatment plan. Further, the patient can get help and find answers to questions via the 3D printed object.

In certain examples, in addition to or alternatively from the 3D printed object, one or more patient portals, web based tools, mobile applications, etc., can be used to provide patient information, goals tracking, monitoring, etc. In certain examples, virtual medical avatars can be used in place of or in conjunction with physical avatars, such as the 3D printed object.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, BLU-RAY®, etc., storing the software and/or firmware.

Patients have a critical role to play in improving health outcomes and in reducing treatment cost, especially in relation to chronic diseases and more complex diseases such as cancer and heart diseases. However, patients must feel empowered and be motivated to participate. Many benefits can arise from improved patient engagement. For example, loyalty and patient confidence levels can be improved by involving the patients in the care process and better coordinate with the care providers. Enhanced patient-physician coordination can improve health outcomes and increase the patient satisfaction. Focusing communication between patient and physician can lead to mutual decision making on the care plan. Virtualization of procedures, such as, electronic medication prescription, online appointment scheduling, etc., can improve communication and deepen a patient's knowledge of the care plan. Further, improved patient engagement promotes shared responsibility of health records' integrity. A patient updating his or her health information lowers data entry cost for physicians. Enhanced engagement improves financial processes and negotiable payment plans.

However, successfully engaging even a small percentage of patients can be challenging. The concept of "If you build it, they will come" has not been working very well. Past attempts have leveraged patient portals and often those attempts ignored some fundamental behavioral traits of the patient population. Patient portals tend to leave behind those who need engagement the most. Elderly and low-income patients with chronic diseases have the highest rate of hospital readmissions. This patient population will not touch patient portals. In addition to patient portals to access information, information and education should be delivered to patients in a frictionless manner. The solutions should be simple, user-friendly, cost effective, holistic and easily accessible to elderly and low-income patients, for example. Success of a patient-centered care model on the technology side depends heavily on availability of solutions that cover patients from all walks of life without any unintentional favoritism towards certain race, gender, income and age.

Certain examples connect consumers (e.g., patients) to advancements in healthcare, such as in molecular medicine and clinical research relevant to their predisposed diseases (e.g., genetically, hereditarily, environmentally, etc., pre-disposed or inclined to suffer from). Furthermore, certain examples provide systems, apparatus, and methods including guidance for a user to seek professional intervention.

Certain examples improve patient engagement for patients with chronic disease such as heart failure, diabetes, osteoporosis, kidney diseases, and complex diseases such as cancer.

Figure 1:
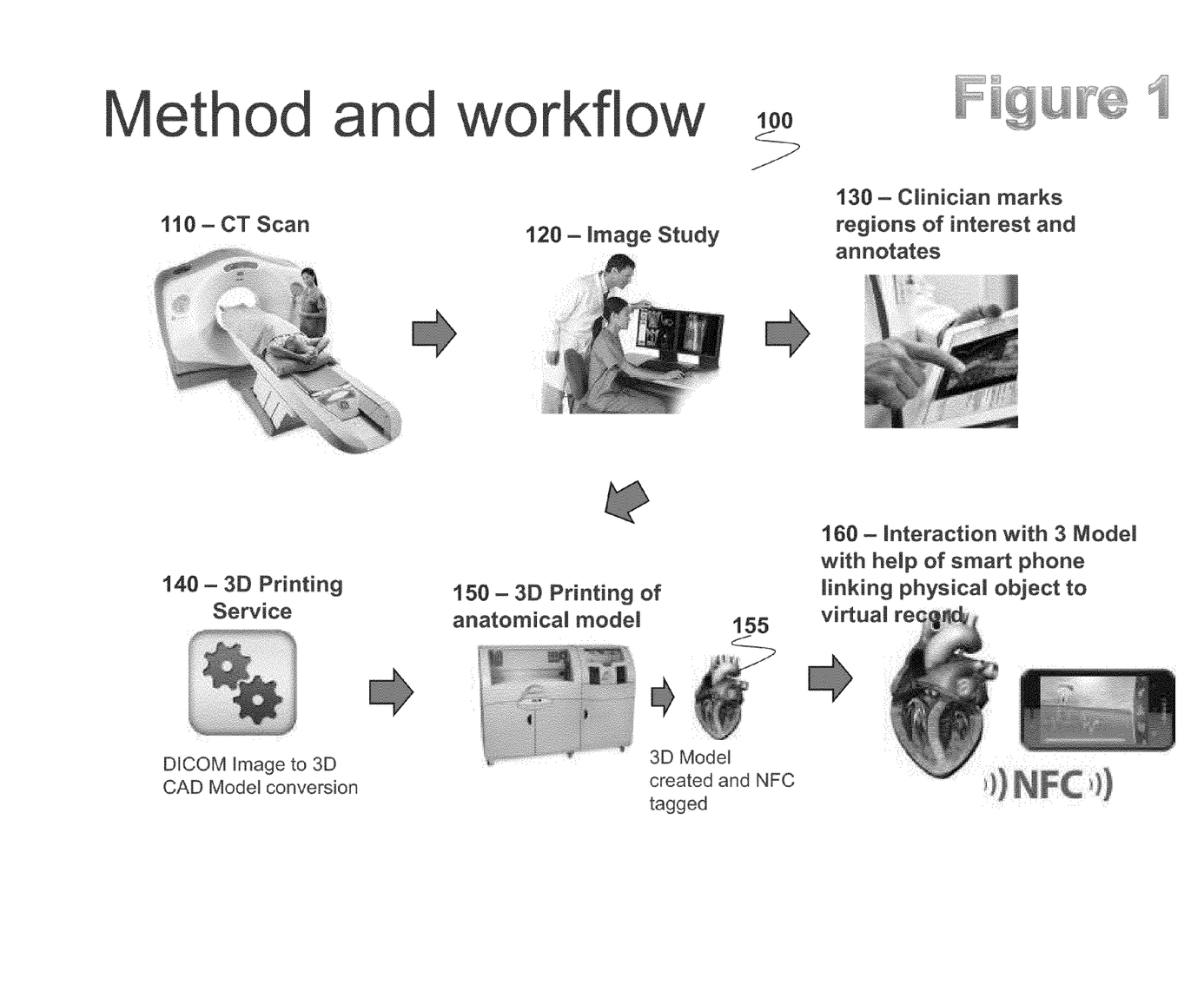
FIG. 1 illustrates a flow diagram for an example method and workflow to facilitate patient treatment using a three-dimensional anatomical model.

FIG. 1 illustrates a flow diagram for an example method and workflow 100 to facilitate patient treatment using a 3D anatomical model. At block 110, a patient is examined. For example, a patient with Congestive Heart Failure (CHF) undergoes an imaging scan, such as a CT scan and/or other imaging scan (e.g., ultrasound, MRI, etc.).

At block 120, examination results are reviewed. For example, an obtained image study is reviewed. At block 130, a clinician annotations and documents the review to develop a treatment plan. For example, after diagnosis of CHF and various image studies, a cardiologist in charge prepares a treatment plan and consults with the patient. CHF requires the patient to take an active role in management of the disease. The active role includes taking medicine as prescribed, avoiding high-salt foods, daily weight-monitoring, controlled exercises, diets, rest between activities, etc. The instructions can be a lot to remember for an elderly patient who has many questions about the disease. The cardiologist shows the patient images of his or her heart that were acquired during the CT scan and reviews the treatment plan, for example.

At block 140, the clinician orders a 3D model relevant to the patient's diagnosis and/or treatment to be printed. For example, the cardiologist orders a 3D model of the patient's heart. A request is sent to a 3D printing service, for example. At block 150, the 3D model is printed. For example, a 3D printer recreates a model of the patient's heart in plastic. At block 155, the model is fitted with some embedded electronics, registered and tagged with an NFC tag or other wireless communicator/indicator, for example. Adding the embedded electronics, including processing and communication capability, turns the model into a "medical avatar". The patient receives the avatar as a souvenir and as a tool to assist with the management of the disease. The medical avatar improves patient engagement, for example.

At block 160, interaction with the 3D model is facilitated with the help of a smart phone or other mobile computing device (e.g., a tablet computer, laptop computer, etc.) linking the physical object to a virtual record. For example, by using a smart phone or tablet, the patient scans the NFC tag embedded in the avatar. This allows the patient to interact with a virtual medical avatar of the patient via a mobile software application.

The physical avatar (e.g., a plastic heart as shown in the example of FIG. 1) has a variety of uses. For example, the physical avatar serves as a portal into a medical care team by providing quick and easy access via the mobile application. Scanning the NFC tag authenticates the user and provides context for the care team and association with the patient's medical record, for example. The physical avatar can educate the patient via the smart phone or other mobile device regarding how to manage the disease and provide access to clinical research and guidelines, for example. The physical avatar allows the patient to ask questions of the care team. The physical avatar serves as a conversation piece with family and friends and can educate them about how to provide support and care for the patient. The physical avatar can provide access to interactive and social games to encourage and challenge to patient to adhere with the treatment plan and guidelines. The physical avatar reminds the patient (e.g., through vibration, sounds, and/or lights, etc.) to comply with tasks as defined in the treatment plan (such as taking medication, exercising, diets, etc.).

Figure 2:
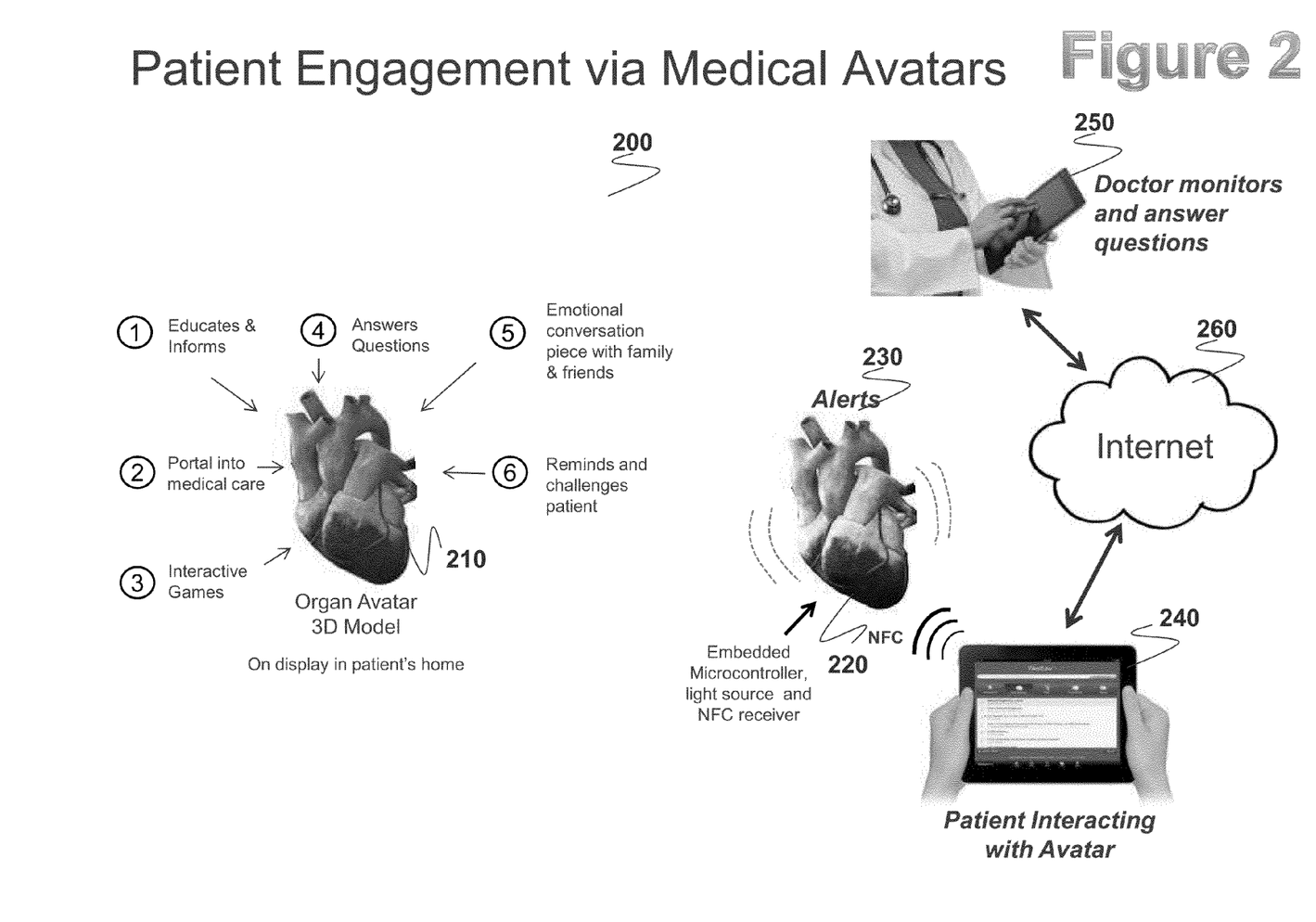
FIG. 2 illustrates an example system and associated data flow to improve patient engagement via a medical avatar.

FIG. 2 illustrates an example system and associated data flow 200 to improve patient engagement via a medical avatar. As shown in the example of FIG. 2, an organ avatar 3D model 210 is associated with a patient and goes home with the patient to be on display in the patient's home. The model 210 provides a variety of information and services to the patient.

For example, the model 210 (1) educates and informs the patient regarding the patient's condition and associated treatment. The model 210 (2) provides a portal into medical care information (e.g., medical care team, clinical knowledge base, best practices, treatment plans, electronic medical record information, etc.). The model 210 (3) provides interactive games to help educate the patient and/or facilitate execution of the patient's care plan, for example. The model 210 (4) answers questions posed by the patient and/or family and friends. The model 210 (5) serves as an emotional conversation piece with family and friends. The model 210 (6) reminds and challenges the patient to adhere to his or her treatment and/or other care plan.

In certain examples, as illustrated in FIG. 2, the model 210 includes an embedded microcontroller, light source and wireless (e.g., NFC) receiver 220 to generate alerts 230 and facilitate interaction between the patient and the avatar via a computing device 240. Additionally, remote interaction with a clinician 250 can be facilitated over a network 260, such as the Internet. The remote clinician 250 can monitor information from the model 210 and answer patient questions, for example.

Figure 3:
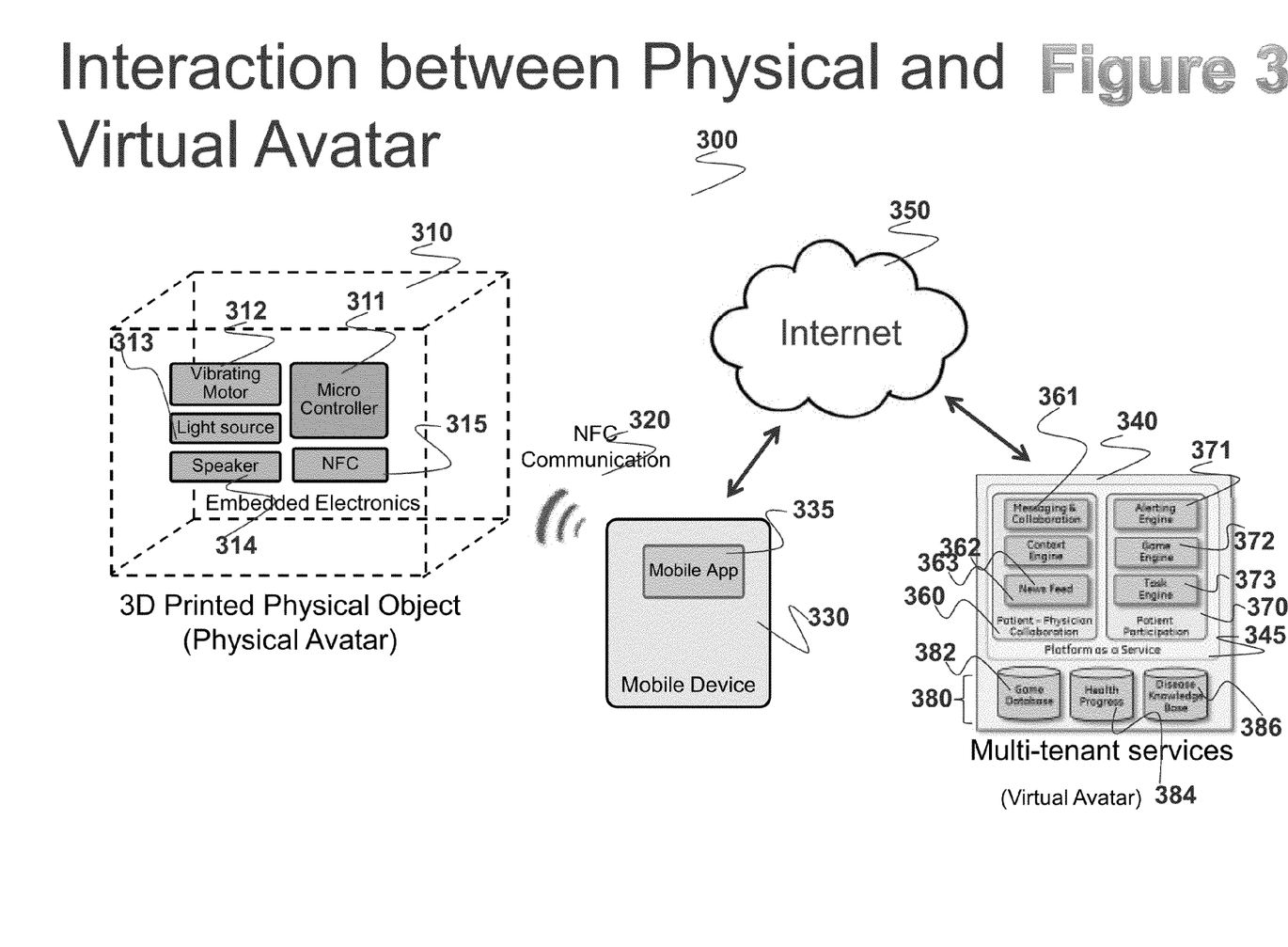
FIG. 3 illustrates an example system and associated data flow to facilitate interaction between a physical avatar and a virtual avatar associated with the patient.

FIG. 3 illustrates an example system and associated data flow 300 to facilitate interaction between a physical avatar and a virtual avatar associated with the patient. For example, FIG. 3 shows how a physical avatar (e.g. a plastic heart, lung, kidney, brain, joints, knees, etc.) interacts with the patient's virtual medical avatar. As shown in the example of FIG. 3, the system 300 includes a physical avatar 310, a mobile device 330, and multi-tenant services 340, for example. The example medical avatar 310 includes an embedded microcontroller 311, a vibrating motor 312, a light source 313, one or more speakers 314, and an NFC tag 315. The medical avatar 310 can represent a part of the patient's anatomy, such as the patient's heart recreated from a CT scan of the patient.

The mobile device 330, such as a smartphone, tablet, laptop, etc., includes a mobile application 335 to allow the patient to interact with a virtual avatar as well as the physical avatar 310. The mobile application 335 relays instructions to embedded electronics in the physical object 310. In the example system 300, the mobile device 330 communicates with the physical avatar 310 via NFC communication 320. Alternatively or in addition, other wired and/or wireless communication channels can be established. The mobile device 330 also communicates with multi-tenant services 340 via a network 350 such as the Internet.

The multi-tenant services 340 realize a virtual avatar for the patient. Multi-tenant services 340 includes tools for patient-physician collaboration 360 and patient participation 370 as part of a platform as a service (PaaS) 345.

Patient-physician collaboration tools 360 include messaging and collaboration 361, a context engine 362, and a news feed 362. The Patient-physician collaboration tools 360 facilitate exchange of communication between the patient and his or her physician as well as a news feed of relevant updates, best practices, alerts, reminders, etc. Such communication and messaging can be provided in the particular patient and/or condition context via the context engine 362, for example.

Patient participation tools 370 include an alerting engine 371, a game engine 372, and a task engine 373. The alerting engine 371 can send alerts to the patient regarding the patient's status, health, care plan, urgent update, etc. The game engine 372 facilitates gamification of the relationship between the patient and his or her condition via the physical avatar 310, for example. The task engine 373 helps the patient with a care or treatment plan involving one or more tasks and reminders regarding the tasks in concert with the physical avatar 310, for example.

One or more data stores 380, such as game database 382, health progress data store 384, disease knowledge base 386, etc., can be provided to store and/or retrieve information for the tools in the platform, for example.

Figure 4:
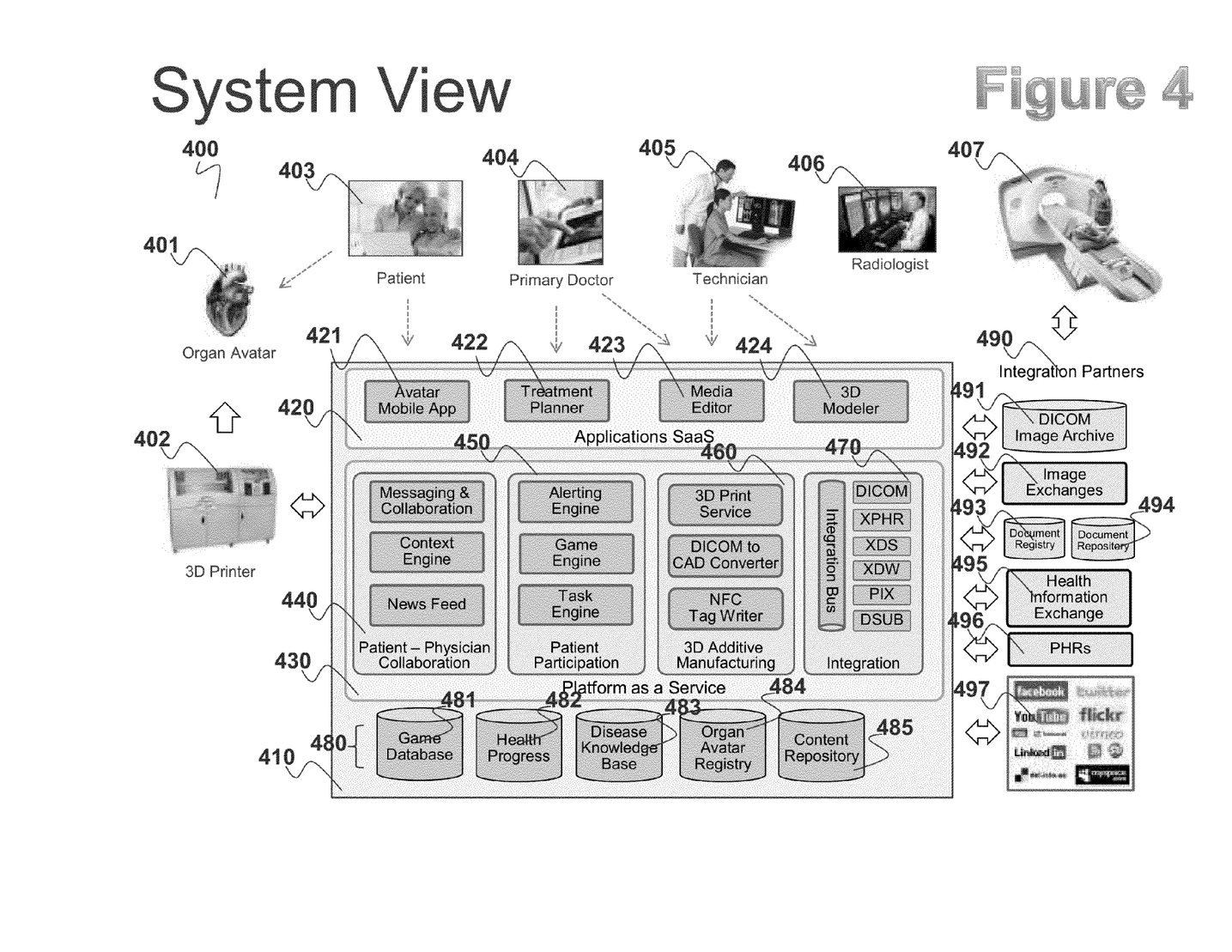
FIG. 4 shows an example system to support and interact with a medical avatar.

FIG. 4 shows an example system 400 to support and interact with a medical avatar. As shown in the example of FIG. 4, the system 400 can provide support and interaction using a cloud based platform and cloud delivered applications. The example system 400 includes a remote support system 410 including one or more applications 420 provided as software as a service (SaaS) as well as a support platform 430 provided as a PaaS.

The applications 420 include an avatar mobile application 421, a treatment planner 422, a media editor 423, and a 3D modeler 424. The avatar mobile application 421 enables a patient to interact with a virtual medical avatar, for example. The treatment planner 422 enables clinicians to create a treatment plan for the patient and an associated game plan for the avatar. The game plan directs the medical avatar regarding how to challenge, coach and alert the patient, for example. The media editor 423 enables medical technicians and specialist to annotate a 3D model and assemble images of the patient and educational information to create the virtual medical avatar of the patient. The 3D modeler 424 is a designer tool that enables medical technicians and specialists to import diagnostic images, such as CT, MR, XRay, and PET/CT images, in DICOM format into a 3D computer-aided design (CAD) model that can be modeled further to develop a physical avatar of a portion of the patient anatomy. The 3D modeler 424 allows a user to print the object using a 3D printer.

The cloud based Platform-as-a-Service 430 includes components to support physician-patient collaboration, patient participation, 3D printing, and integration with external systems, for example. For example, the platform 430 includes patient-physician collaboration tools 440, patient participation tools 450, 3D manufacturing tools 460, and integration tools 470.

Patient-physician collaboration tools 440 include messaging and collaboration, a context engine, and a news feed. The Patient-physician collaboration tools 440 facilitate exchange of communication between the patient and his or her physician as well as a news feed of relevant updates, best practices, alerts, reminders, etc. Such communication and messaging can be provided in the particular patient and/or condition context via the context engine, for example.

Patient participation tools 450 include an alerting engine, a game engine, and a task engine. The alerting engine can send alerts to the patient regarding the patient's status, health, care plan, urgent update, etc. The game engine facilitates gamification of the relationship between the patient and his or her condition via the physical avatar, for example. The task engine helps the patient with a care or treatment plan involving one or more tasks and reminders regarding the tasks in concert with the physical avatar, for example.

The 3D manufacturing tools 460 include a 3D print service, a DICOM to CAD converter, and an NFC tag writer. The 3D manufacturing tools 460 work with a 3D printer 402 to print a physical avatar 401 based on patient information, processing, and communication capability, for example.

The integration tools 470 facilitate integration with one or more external systems via healthcare standards, such as DICOM, HL7, and IHE profiles (e.g., XPHR, XDS, XDW, PIX, and DSUB). Via the integration tools 470, the support system 410 can communicate and exchange information with one or more integration partners 490, such as an image archive 491 (e.g., DICOM image archive), image exchange 492, document registry 493, document repository 494, health information exchange (HIE) 495, personal health record (PHR) 496, web page 497, etc.

The remote support system 410 can include one or more data stores 480 such as a game database 481, health progress tracker 482, disease knowledge base 483, organ avatar registry 484, and content repository 485. The data stores 480 store and provide data to the platform 430 and/or applications 420, for example.

As illustrated in the example of FIG. 4, one or more users can interact with components of the system 400. For example, a patient 403 interacts with the physical avatar 401 as well as the remote support system 410. A primary physician 404 for the patient 403 also interacts with the remote support system 410. Other clinicians/healthcare practitioners, such as a technician 405, a radiologist 406, etc., can interact with the remote support system 410 to provide and/or retrieve information and/or services, for example. One or more clinical devices such as medical imagers 407 can also interact with the integration partners 490 to provide information, such as images, to the integration partners 490 and ultimately, in at least some cases, to the support system 410 (e.g., to provide image data to print the 3D physical avatar 401, provide supporting information for a virtual avatar, etc.).

Via the physical avatar 401 and the patient's mobile device, the patient can benefit from interaction with the physical avatar 401 as well as supporting information in the form of a virtual avatar backing the physical avatar 401 based on the remote support system 401.

The following is an example scenario presented for purposes of illustration only. This scenario involving care of a cardiac patient is but one of many examples that will be clear to one of ordinary skill in the art after reading and understanding the description above. However, for brevity, the following example is provided. The example scenario is for a cardiac patient who is being treated for a heart condition. To being his treatment, CT images are obtained for the patient, along with electrocardiogram readings and other vital sign readings at a local hospital. Based on the gathered information, a 3D printer is used to generate a physical model of the patient's heart (a physical avatar).

The patient is discharged and returns home with his or her physical avatar and a care plan for his or her heart condition. The physical avatar helps the patient follow a schedule and reminds the patient to complete certain tasks. If the plan is not followed, the physical avatar can generate an alert for the patient, for example. Additionally, the physical avatar and an associated virtual avatar backed by a remote platform and applications can be used as resources to help the patient via a mobile device, such as a smart phone, tablet computer, laptop computer, etc. Communication with the patient's physician, updates on latest care practices and other relevant news, reporting to a healthcare facility, etc., can be facilitated using the physical and virtual avatars, for example.

Thus, certain examples can help navigate a patient's care plan and health monitoring. Certain examples can help facilitate an ongoing dialog between the patient and one or more care providers without repeated visits to a healthcare facility. Certain examples help ensure better prepared patient discharge as well as post-discharge follow-up and intervention, etc.

While the above scenario is one example complex case, there are numerous other scenarios which can be described and where the systems and associated methods described above and illustrated in the drawings play an important role in improving the patient outcome.

The above flowcharts and data flow diagrams can be representative of example machine readable instructions for implementing the example systems and methods described herein. In these examples, the machine readable instructions comprise a program for execution by a processor such as the processor 512 shown in the example processor platform 500 discussed below in connection with FIG. 5. The program may be embodied in software stored on a tangible computer readable medium such as a compact disc read-only memory ("CD-ROM"), a floppy disk, a hard drive, a digital video disc (DVD), Blu-ray disk, or a memory associated with the processor 512, but the entire program and/or parts thereof could alternatively be executed by a device other than the processor 512 and/or embodied in firmware or dedicated hardware. Further, although the example program is described with reference to the present figures and associated description, many other methods of implementing the example systems, etc., may alternatively be used. For example, the order of execution of the blocks may be changed, and/or some of the blocks described may be changed, eliminated, or combined.

As mentioned above, the example processes described herein can be implemented using coded instructions (e.g., computer readable instructions) stored on a tangible computer readable medium such as a hard disk drive, a flash memory, a read-only memory ("ROM"), a CD, a DVD, a Blu-Ray, a cache, a random-access memory ("RAM") and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

Figure 5:
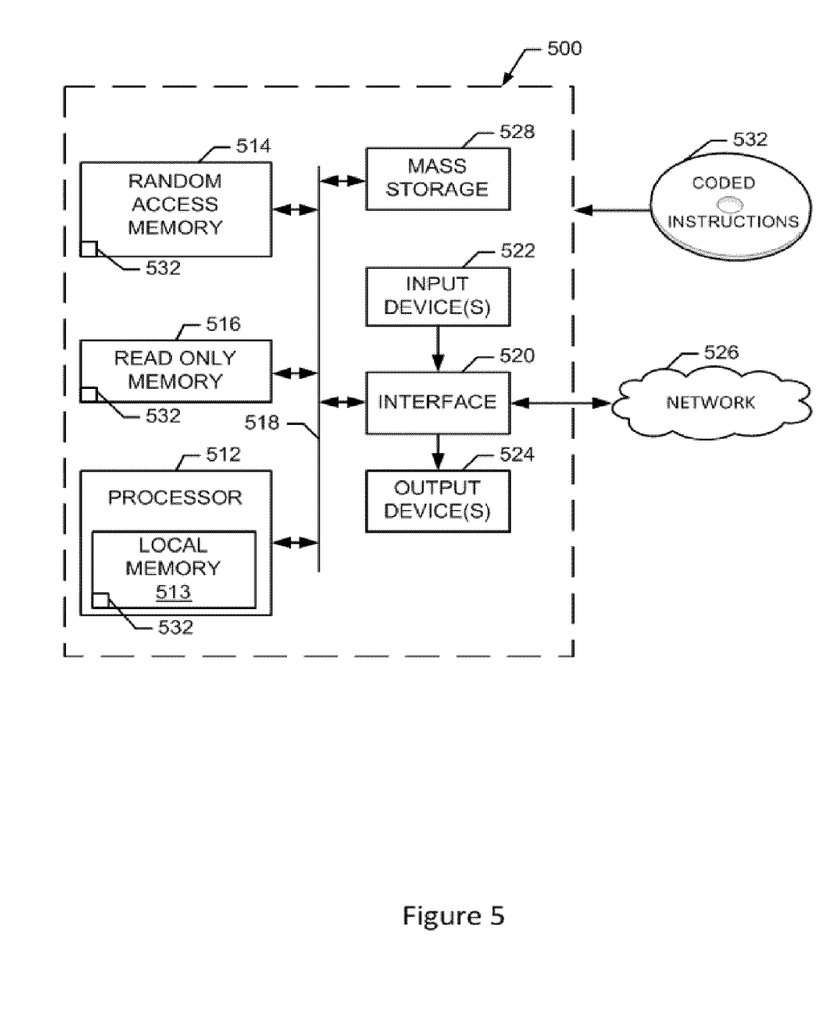
FIG. 5 is a block diagram of an example processor platform capable of implementing methods, systems, apparatus, etc., described herein.

FIG. 5 is a block diagram of an example processor platform 500 capable of executing instructions of the example systems and methods described herein. The processor platform 500 can be, for example, a server, a personal computer, an Internet appliance, a set top box, or any other type of computing device.

The processor platform 500 of the instant example includes a processor 512. For example, the processor 512 can be implemented by one or more microprocessors or controllers from any desired family or manufacturer. The processor 512 includes a local memory 513 (e.g., a cache) and is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The processor platform 500 also includes an interface circuit 520. The interface circuit 520 may be implemented by any type of interface standard, such as an Ethernet interface, a universal serial bus (USB), and/or a PCI express interface.

One or more input devices 522 are connected to the interface circuit 520. The input device(s) 522 permit a user to enter data and commands into the processor 512. The input device(s) can be implemented by, for example, a keyboard, a mouse, a touchscreen, a track-pad, a trackball, isopoint and/or a voice recognition system.

One or more output devices 524 are also connected to the interface circuit 520. The output devices 524 can be implemented, for example, by display devices (e.g., a liquid crystal display, a cathode ray tube display (CRT), etc.). The interface circuit 520, thus, typically includes a graphics driver card.

The interface circuit 520 also includes a communication device such as a modem or network interface card to facilitate exchange of data with external computers via a network 526 (e.g., an Ethernet connection, a digital subscriber line (DSL), a telephone line, coaxial cable, a cellular telephone system, etc.).

The processor platform 500 also includes one or more mass storage devices 528 for storing software and data. Examples of such mass storage devices 528 include floppy disk drives, hard drive disks, compact disk drives and digital versatile disk (DVD) drives. The mass storage device 528 may implement a local storage device.

The coded instructions 532 may be stored in the mass storage device 528, in the volatile memory 514, in the non-volatile memory 516, and/or on a removable storage medium such as a BLU-RAY, CD or DVD.

Although certain example methods, systems, apparatus, and articles of manufacture have been described herein, the scope of coverage of this patent is not limited thereto. On the contrary, this patent covers all methods, systems and articles of manufacture fairly falling within the scope of the claims of this patent.

The invention claimed is:

1. An apparatus comprising:
   a three-dimensional printed model of a portion of a patient anatomy, the three-dimensional printed model formed for the patient based on image data obtained of the patient, the three-dimensional printed model comprising:
      an output device to provide an output from the three-dimensional printed model that is perceptible to the patient;
      a communication device to facilitate exchange of information between the three-dimensional printed model and one or more external systems; and
      a controller to facilitate exchange of information, via the communication device, between the three-dimensional printed model and the one or more external systems, the controller also to provide feedback to the patient via the output device with respect to a condition affecting the portion of the patient anatomy represented by the three-dimensional printed model via the output device.

2. The apparatus of claim 1, wherein the output device comprises at least one of a vibrating motor, a light source, and a speaker.

3. The apparatus of claim 1, wherein the output device is to provide an alert with respect to the three-dimensional printed model to remind the patient regarding the condition.

4. The apparatus of claim 1, wherein the communication device comprises a near field communication device.

5. The apparatus of claim 1, wherein the three-dimensional printed model is to be formed by a three-dimensional printer based on input from image data and electronic medical information related to the patient.

6. The apparatus of claim 1, wherein the one or more external systems include a mobile device, the mobile device to communicate with the three-dimensional printed model to link the three-dimensional printed model to a virtual record associated with the patient.

7. The apparatus of claim 6, wherein the mobile device is to facilitate interaction between the patient and a care provider in conjunction with the three-dimensional printed model.

8. The apparatus of claim 6, wherein the one or more external systems include a remote support system, the remote support system to operate with the mobile device to provide the virtual record corresponding to the three-dimensional printed object.

9. A system comprising:
- a three-dimensional printed avatar representing a portion of a patient anatomy, the three-dimensional printed avatar formed for the patient based on image data obtained of the patient, the three-dimensional printed avatar comprising:
  - an output device to provide an output from the three-dimensional printed avatar that is perceptible to the patient;
  - a communication device to facilitate exchange of information between the three-dimensional printed avatar and one or more external systems; and
  - a controller to facilitate exchange of information, via the communication device, between the three-dimensional printed avatar and the one or more external systems, the controller also to provide feedback to the patient via the output device with respect to a condition affecting the portion of the patient anatomy represented by the three-dimensional printed avatar via the output device; and
- a remote services platform providing applications and platform services to form a virtual avatar corresponding to the three-dimensional printed avatar, the remote services platform communicating with the three-dimensional printed avatar via a mobile device associated with the patient, the remote services platform to provide support for three-dimensional modeling, messaging with the patient, and integration with external systems.

10. The system of claim 9, wherein the remote services platform comprises patient-physician collaboration tools, patient participation tools and integration tools.

11. The system of claim 10, wherein the patient-physician collaboration tools comprise at least one of messaging and collaboration tools, a context engine, and a news feed.

12. The system of claim 10, wherein the patient participation tools comprise at least one of an alerting engine, a game engine, and a task engine.

13. The system of claim 10, wherein the remote services platform further comprises three-dimensional manufacturing tools.

14. The system of claim 9, wherein the output device comprises at least one of a vibrating motor, a light source, and a speaker.

15. The system of claim 9, wherein the communication device comprises a near field communication device.

16. The system of claim 9, wherein the three-dimensional printed avatar is to be formed by a three-dimensional printer based on input from image data and electronic medical information related to the patient.

17. A tangible computer-readable storage medium including a set of instructions to be executed by a processor, the instructions, when executed, implementing a method, the method comprising:
- generating three-dimensional model information to print a physical avatar on a three-dimensional printer, the physical avatar to model a portion of a particular patient's anatomy based on image data obtained of the particular patient, the physical avatar to include an output device to provide an output from the physical avatar that is perceptible to the patient, a communication device to facilitate exchange of information between the physical avatar and one or more external systems, and a controller to facilitate exchange of information, via the communication device, between the physical avatar and the one or more external systems;
- facilitating an exchange of information related to the patient between the physical avatar and the one or more external systems that provide a virtual avatar, the virtual avatar providing messaging, information and patient participation tools to facilitate patient engagement in monitoring and treatment of a condition affecting the portion of the patient anatomy represented by the physical avatar, the exchange of information including alerts provided by the output device in response to information from the virtual avatar.

18. The method of claim 17, wherein the three-dimensional model information is based on electronic medical information related to the patient as well as image data related to the patient.

19. The method of claim 17, further comprising facilitating exchange of information between the physical avatar, the virtual avatar, and a mobile device associated with the patient, wherein the mobile device is to facilitate interaction between the patient and a care provider in conjunction with the three-dimensional printed model.

20. The method of claim 17, further comprising providing at least a portion of the method via a cloud-based platform.

* * * * *